United States Patent
Amato

(10) Patent No.: US 7,862,626 B2
(45) Date of Patent: Jan. 4, 2011

(54) FATTY PHASE FOR THE PREPARATION OF HAIR DYES, PROCEDURE FOR THE PREPARATION OF SAID FATTY PHASE AND SYSTEM FOR CARRYING OUT SAID PROCEDURE

(75) Inventor: George Amato, Mriehel (MT)

(73) Assignees: Industrial Chemical Cosmetics Limited, Marsa (MT); Beauty & Business S.r.l., Milan (IT)

( * ) Notice: Subject to any disclaimer, the term of this patent is extended or adjusted under 35 U.S.C. 154(b) by 0 days.

(21) Appl. No.: 12/573,412

(22) Filed: Oct. 5, 2009

(65) Prior Publication Data

US 2010/0083447 A1    Apr. 8, 2010

(30) Foreign Application Priority Data

Oct. 6, 2008    (MT) .......................................... 4233

(51) Int. Cl.
*A61Q 5/10*    (2006.01)

(52) U.S. Cl. .................. 8/405; 8/435; 8/580; 8/611
(58) Field of Classification Search .................... 8/405, 8/435, 580, 611
See application file for complete search history.

(56) References Cited

U.S. PATENT DOCUMENTS

2006/0075580 A1*   4/2006   Chan et al. .................... 8/405

* cited by examiner

*Primary Examiner*—Eisa B Elhilo
(74) *Attorney, Agent, or Firm*—Young & Thompson

(57) ABSTRACT

A fatty phase for the preparation of hair dyes, consisting of a semi-finished product containing the proportions of stearyl and cetyl alcohols suitable for the preparation of the dye. In relation to the prior art, the invention allows a semi-finished product for preparation of hair dyes to be obtained, consisting of a fatty phase with the ingredients already measured out and mixed, so as to be ready to be integrated, inside the mixer, with the remaining components (colorants, etc.) that make up the final formulation of the dye.

9 Claims, 2 Drawing Sheets

FATTY PHASE FOR THE PREPARATION OF HAIR DYES, PROCEDURE FOR THE PREPARATION OF SAID FATTY PHASE AND SYSTEM FOR CARRYING OUT SAID PROCEDURE

The present invention concerns a fatty phase for the preparation of hair dyes. The invention also extends to the procedure used to prepare this fatty phase and to the system for carrying out said procedure.

The field of the invention is that of hair dyes, which comprise a solution of colorants dispersed in a so-called fatty phase, the latter suitable to give the dyes the most appropriate pasty or creamy consistency for application to the hair. Preparation of these dyes is carried out in a mixer where all the components are added, that is, those that form the fatty phase, the other raw materials and the colorants previously dissolved hot in a mixer.

The above described prior art has the drawback of requiring preparation of the individual components of the fatty phase, which are added one by one in the final dye preparation mixer. As a result, the formulation of this fatty phase is known to the operators, thus losing any bonds of secrecy.

Furthermore, the operation requires weighing of all the individual components of the fatty phase at the time of preparation of the dye.

The above mentioned prior art also has the drawback of slowing down the dye manufacturing cycle because of the necessary operation of measuring out the fatty phase and handling the numerous raw materials that are involved.

The main object of the present invention is to make the operations involved in preparation of the dye faster, simpler and safer, at the same to maintain the secrecy of the formulation.

This and other objects are achieved with the fatty phase, the procedure, the system and the dye of claims 1, 4, 7 and 10, respectively. Preferred embodiments of the invention are apparent from the remaining claims.

In relation to the prior art, the invention allows a semi-finished product for preparation of hair dyes to be obtained, consisting of a fatty phase with the ingredients already measured out and mixed, so as to be ready to be integrated, inside the mixer, with the remaining components (colorants, etc.) that make up the final formulation of the dye.

The secrecy of the formulation of the fatty phase is thus guaranteed, in that it is prepared outside the factory where the final dye is prepared. Furthermore, correct measuring out of the ingredients in this fatty phase is guaranteed by preparation thereof inside the specific structure set up to make it. Lastly the overall procedure for preparation of the dye is made faster and safer by immediate access to the semi-finished product, ready for use in the desired amounts. As a general rule, it can therefore be stated that the availability of a semi-finished fatty phase product ensures the consistent quality of the end product, which has been given the most suitable physico-chemical characteristics for the desired application.

These and other objects, advantages and characteristics will emerge from the description that follows of a preferred method for creating the system of the invention, illustrated, by way of non limiting example, in the figures of the appended plates of drawings. In these:

Figure 1:
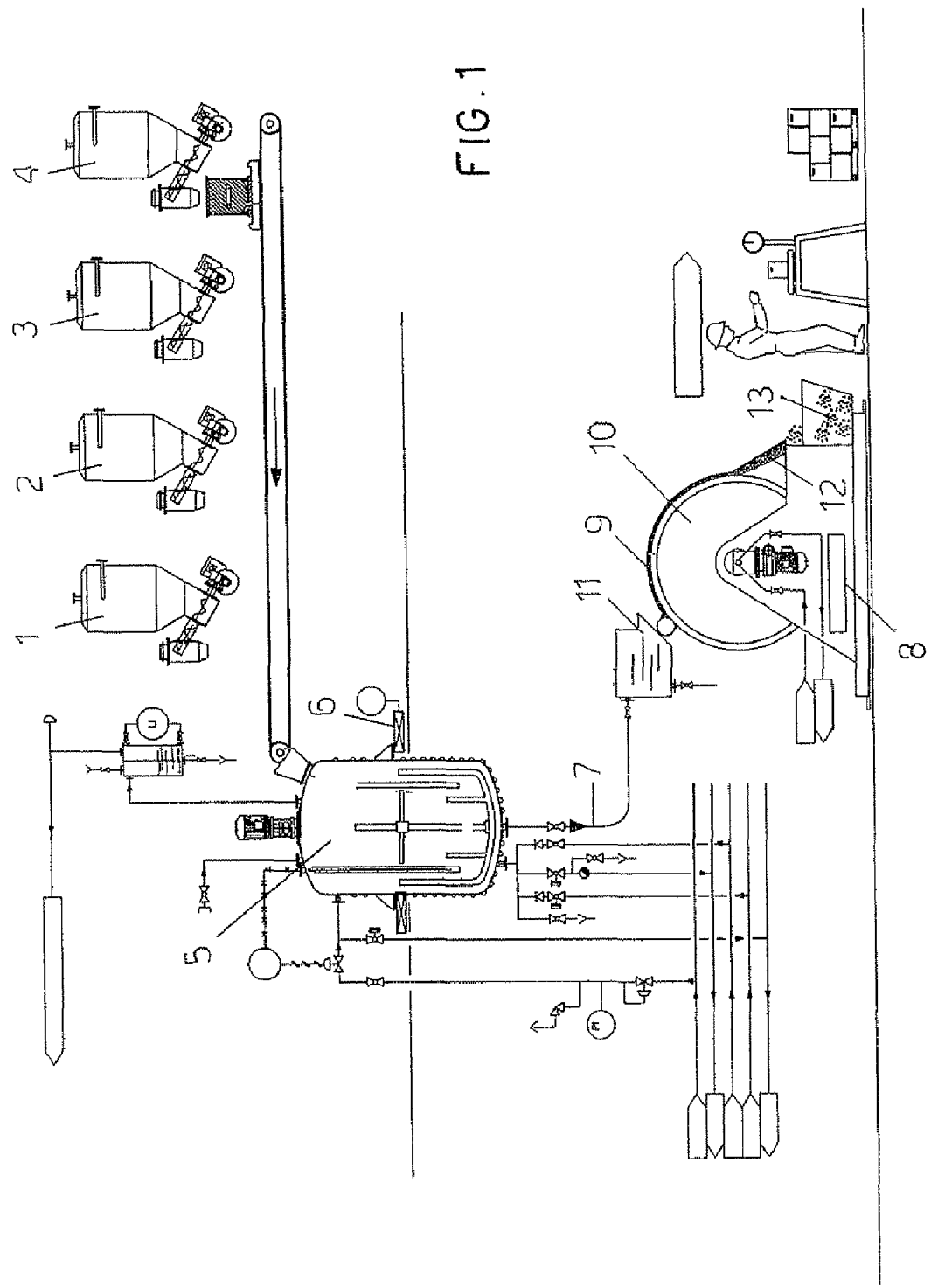
FIG. 1 is a diagrammatic overall view of the system of the invention.

The system illustrated in FIG. 1 comprises the holding bins 1 and 4 for the individual ingredients that form the fatty phase for hair dyes, that is:

cetyl stearyl alcohol C16, C18 in a ratio of 30/70 by weight
cetyl stearyl alcohol C16, C18 in a ratio of 70/30 by weight stearyl alcohol;
cetyl stearyl alcohol with ethylene oxide added.

These ingredients are generally characterised by the presence of cetyl (C16) and stearyl (C18) alcohol, in suitable proportions to obtain the desired mixture. For example, this can be composed:

from 17% to 22%, of a mixture of cetyl stearyl alcohol C16/C17 at 30/70% by weight;
from 20% to 25%, of a mixture of cetyl stearyl alcohol C16/C17 at 70/30% by weight;
from 32% to 37%, of stearyl alcohol C18
from 20% to 25%, of a cetyl stearyl alcohol based emulsifier with 50 moles of ethylene oxide.

All these raw materials, having a melting point of 55-60° C., are loaded individually into a heated mixer 5, according to the pre-set proportions, with weighing carried out starting from a load cell 6 on the bottom of said mixer.

Once the desired degree of measuring out of the fatty phase under way has been reached, heating to a machine temperature of about 80-85° C. is begun, so as to bring the ingredients to a molten, completely mixed state. A homogeneous liquid 7 is thus obtained which, after checking with a gas chromotograph, is conveyed to the flaking system.

The latter is composed in particular of a cylinder 10 cooled on the inside to a temperature of about 5° C., on the outer surface of which a thin layer 9 of the molten liquid 7 is deposited through a hopper 11. The mixture of fatty alcohols solidifies due to the low temperature of the surface of the cylinder and is removed by a blade 12, disposed at a tangent to the surface of the cylinder 10. Flakes 13 of fatty phase are thus obtained.

Figure 2:
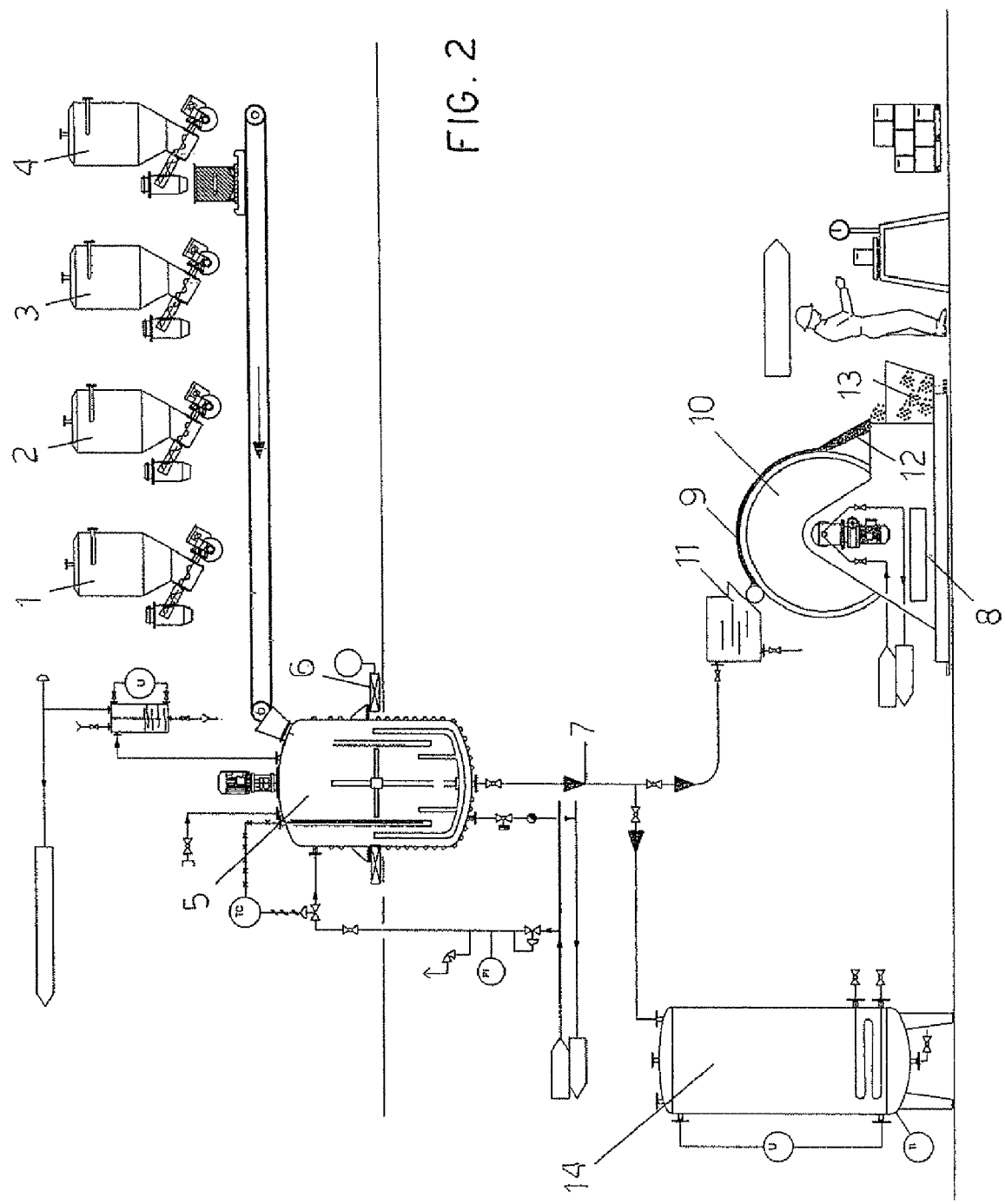
FIG. 2 shows a variant embodiment of the system of FIG. 1.

The above described procedure of the invention allows both the fatty phase in flake form 13, suitably packaged in bags, and the molten product 7 leaving the mixer 5 and collected in a heated tank 14 (FIG. 2) to be used.

The latter variant is preferred, in that it offers the possibility of automating the overall dye making process, by loading the individual ingredients without any need for operator intervention on the packages of fatty phase in flakes.

Obviously the invention is not limited to the above described embodiment, it being possible, for example, to vary the amounts of the components that make up the fatty phase.

The invention claimed is:

1. A composition for preparation of hair dyes, comprising a combination of an emulsifier and a fatty phase consisting of a semi-finished product containing stearyl and cetyl alcohols in a proportion suitable for the preparation of said dyes.

2. The combination according to claim 1, wherein,
the fatty phase consists of the stearyl and cetyl alcohols as a mixture of cetyl stearyl alcohol C16/C18 at 30/70% by weight, cetyl stearyl alcohol C16/C18 at 70/30% by weight, and a stearyl alcohol C18; and
the emulsifier is a cetyl stearyl alcohol based emulsifier with ethylene oxide.

3. A procedure for preparation of the fatty phase according to claim 1, consisting of:
(a) measuring out the individual cetyl and stearyl alcohols inside a heated mixer; and
(b) obtaining a molten mass of fatty phase from said heated mixer.

4. The procedure according to claim 3, wherein said molten mass is used as is in the preparation of the dye.

5. A procedure for the preparation of the fatty phase according to claim 1, consisting of:
   (a) measuring out the individual cetyl and stearyl alcohols inside a heated mixer;
   (b) obtaining a molten mass of fatty phase from said heated mixer; and
   (c) transforming said molten mass of fatty phase into flakes.

6. A system for carrying out the procedure according to claim 3, comprising:
   one or more raw material holding bins for holding raw materials of stearyl and cetyl alcohols;
   a heated mixer for mixing and melting said raw materials to prepare said fatty phase in a molten state; and
   a device for measuring out said raw materials into said mixer.

7. The system according to claim 6, further comprising a flaking system for transforming the fatty phase, in the molten state leaving said mixer, into flakes suitably packaged in bags.

8. The system according to claim 6, further comprising a heated tank for collecting said fatty phase in the molten state.

9. A hair dye, comprising the composition according to claim 1.

* * * * *